(12) United States Patent
Fedida

(10) Patent No.: US 6,402,760 B1
(45) Date of Patent: Jun. 11, 2002

(54) DEVICE FOR CAUSING THE RELEASE OF AN OBJECT, PARTICULARLY A PROSTHESIS, INTO A HUMAN OR ANIMAL PASSAGE, AND IMPLANTATION SYSTEM COMPRISING A CATHETER AND SUCH A DEVICE

(75) Inventor: José Fedida, Mouans-Sartoux (FR)

(73) Assignee: Novatech SA, Grasse le Plan (FR)

( * ) Notice: Subject to any disclaimer, the term of this patent is extended or adjusted under 35 U.S.C. 154(b) by 0 days.

(21) Appl. No.: 09/526,544

(22) Filed: Mar. 16, 2000

(30) Foreign Application Priority Data

Aug. 24, 1999 (FR) .............................. 99 10733

(51) Int. Cl.[7] .............................................. A61M 25/01
(52) U.S. Cl. ...................................... 606/108; 604/528
(58) Field of Search .................... 606/108, 1; 623/1.11; 604/528, 159, 164.01

(56) References Cited

U.S. PATENT DOCUMENTS

| | | | | |
|---|---|---|---|---|
| 3,750,667 A | * | 8/1973 | Pshenichny et al. | 606/108 |
| 5,176,647 A | * | 1/1993 | Knoepfler | 604/158 |
| 5,256,149 A | * | 10/1993 | Banik et al. | 604/158 |
| 5,391,172 A | * | 2/1995 | Williams et al. | 606/108 |
| 5,433,723 A | * | 7/1995 | Lindenberg et al. | 606/198 |
| 5,534,007 A | | 7/1996 | St. Germain et al. | |
| 5,707,376 A | * | 1/1998 | Kavteladze et al. | 606/108 |
| 5,968,052 A | * | 10/1999 | Sullivan, III et al. | 606/108 |

FOREIGN PATENT DOCUMENTS

| | | |
|---|---|---|
| DE | 29717110 U1 | 1/1998 |
| EP | 0418677 A1 | 3/1991 |
| EP | 0461791 A1 | 12/1991 |
| EP | 0536610 A1 | 4/1993 |
| EP | 0880948 A1 | 12/1998 |
| WO | 9521592 | 8/1995 |

* cited by examiner

Primary Examiner—Nicholas D. Lucchesi
Assistant Examiner—Eduardo C. Robert
(74) Attorney, Agent, or Firm—Stevens, Davis, Miller & Mosher, LLP (57) ABSTRACT

Release of an object into a human or an animal passage is performed via a catheter formed of telescopic first and second sheaths. The catheter is at least partially inserted into the passage to release the object in response to relative sliding of the first and second sheaths. The catheter includes a first fixing device that fixes an extra-corporal part of the first sheath to a casing and a second fixing device that fixes an extra-corporal part of the second sheath to a mobile carriage mounted on the casing. A controllable motor moves the mobile carriage with respect to the casing.

22 Claims, 6 Drawing Sheets

DEVICE FOR CAUSING THE RELEASE OF AN OBJECT, PARTICULARLY A PROSTHESIS, INTO A HUMAN OR ANIMAL PASSAGE, AND IMPLANTATION SYSTEM COMPRISING A CATHETER AND SUCH A DEVICE

FIELD OF THE INVENTION

The present invention relates to a device for causing the release of an object, particularly a prosthesis, into a human passage or animal passage and to an implantation system comprising such a device and a catheter carrying the object.

Although not exclusively, the present invention applies more particularly to the implanting of a prosthesis in an artery of the human body, especially in the abdominal aorta.

BACKGROUND OF THE INVENTION

It is known that the implantation of arterial prostheses, such as those disclosed for example in documents EP-0 461 791, WO-95/21592 and EP-0 880 948, is generally performed using a catheter which in particular, and in the known way, comprises:

- a carrying sheath which, at its distal part, comprises dilating means, for example a dilation tip with or without an inflatable balloon, and which carries said prosthesis;
- a pushing intermediate sheath which partially surrounds said carrying sheath and which can slide with respect to the latter; and
- a protective outer sheath which at least partially covers the distal end of said carrying sheath, which partially surrounds said intermediate sheath, and which can slide with respect to the latter.

In the known way, implanting the prosthesis in an artery generally involves the following three successive stages, which may, in particular, be monitored by radiography, for example by providing radio-opaque elements on the catheter and/or the prosthesis:

- an initial stage, during which the prosthesis is brought at least close to its future location in the artery, using the catheter, the aforementioned three sheaths of which are secured together. By way of an illustration, to implant a bifurcated aortic prosthesis, for example of the type described in document EP-0 461 791, in the abdominal aorta between the iliac arteries and the renal arteries, the catheter is generally entered into the human body at the femoral arteries, and the distal part of said catheter, which carries the prosthesis, is brought into the aorta via the iliac arteries;
- a release stage, during which the prosthesis is released into the artery. To do this, the protective outer sheath has, in particular, to be slid with respect to the intermediate sheath so that said outer sheath releases the distal part of the catheter, particularly the region in which the prosthesis is located; and
- a stage of withdrawing the catheter from the human body.

The present invention is concerned more specifically, although not exclusively, with said release stage.

In general, to carry out this release stage, the surgeon implanting the prosthesis, or one of his assistants, manually slides the outer sheath with respect to the intermediate sheath by taking hold of two extracorporal parts of said sheaths, so as to release the prosthesis as discussed hereinabove.

As this operation is performed manually and thus, in general, jerkily, this sliding (and therefore also the release of the prosthesis) is imprecise and uneven. What is more, it is difficult, and sometimes even impossible, to achieve because:

- the sheaths are generally slippery; and, above all,
- it is necessary to produce a great deal of force, particularly to release large prostheses, such as the aforementioned bifurcated aortic prostheses.

SUMMARY OF THE INVENTION

The object of the present invention is to overcome these drawbacks. This invention relates to a device allowing an object, particularly a prosthesis, to be released easily in a human or animal passage in a precise and jerk-free way carrying no risk of injuring said passage, said object being carried and delivered into said human passage or animal passage by a catheter which comprises a first sheath and a second sheath (an intermediate sheath and a protective outer sheath in the aforementioned example) which are partially introduced into said passage, mounted telescopically and able to slide one with respect to the other, which catheter releases said object in response to an appropriate relative sliding of said first and second sheaths.

To this end, according to the invention, said device is noteworthy in that it comprises:

- a casing;
- first fixing means capable of fixing an extracorporal part of said first sheath to said casing;
- a mobile carriage mounted on said casing so that it can be moved with respect thereto;
- second fixing means capable of fixing an extracorporal part of said second sheath to said mobile carriage; and
- controllable drive means capable of moving said mobile carriage with respect to said casing.

Thus, by virtue of the invention, the relative sliding of said first and second sheaths is performed by the device according to the invention. More specifically, this sliding is brought about by moving the mobile carriage (to which one sheath is fixed) with respect to the casing (to which the other sheath is fixed). This is achieved automatically or by generating a small force (depending on the embodiment of drive means considered, as specified hereinbelow) with nothing in common with the aforementioned force that has customarily to be exerted by a surgeon without the use of the device according to the invention.

In consequence, as will be seen in greater detail hereinbelow, the object may be released:

- continuously and smoothly, that is to say without jerkiness;
- without the risk of injuring the passage; and
- very precisely, and this can be achieved purely and simply by mastering the movement of said mobile carriage.

In the context of the present invention, the drive means used for this purpose may be produced in different ways. In particular, and advantageously:

- in a first embodiment, said drive means comprise an endless screw which collaborates with a tapping made in the carriage and which is moved by a controllable motor;
- in a second embodiment, said drive means comprise a rack system which acts on the carriage and which is also moved by a controllable motor;
- in a third embodiment, said drive means comprise:
    - an elastic means, preferably a spring, which is mounted so that it is elastically constrained between the casing and the carriage so as to be able to move the latter with respect to said casing; and a controllable stop capable of preventing the movement of said mobile carriage with respect to said casing; and in a fourth embodiment, said drive means comprise a lever system which can be actuated or controlled manually.

Furthermore, in said first and second embodiments, said motor, preferably a battery-powered or mains-powered electric motor, may be controlled automatically by a programmable element, for example an electronic chip. In this case, the release stage may be performed automatically, according to a pre-established program.

Furthermore, advantageously, said carriage is mounted so that it can move on guide rails, preferably rectilinear guide rails, secured to said casing.

What is more, according to the invention and advantageously, the casing of said device:

has a transparent window allowing part (located inside said casing) of at least one of said sheaths to be seen from the outside, which makes it possible to visually monitor the relative sliding of the two sheaths, and therefore the progress of the stage of releasing said object; and/or is made in two parts which are at least partially separable and which can be secured together, which makes it easy to mount a catheter in said casing and therefore in the device according to the invention; and/or has an elongate shape comprising a handgrip region tailored to the hand of someone using said device, which in particular makes said device easier to hold in the hand and manipulate.

The present invention also relates to a system for implanting an object, particularly a prosthesis, in a human passage or animal passage, particularly in an artery.

According to the invention, said system is noteworthy in that it comprises:

a catheter which:

carries and delivers said object into said human passage or animal passage;

comprises a first sheath and a second sheath which can be partially introduced into said passage, mounted telescopically and able to slide one with respect to the other; and releases said object in response to an appropriate relative sliding of said first and second sheaths; and a device like the aforementioned one, for causing the release of said object in said human passage or animal passage by causing said relative sliding of the first and second sheaths.

Furthermore, advantageously, at least one of said sheaths comprises an anti-reflux valve, which makes it possible, when implanting in an artery or blood vessel, to prevent blood from flowing out of said artery or blood vessel via said catheter.

Furthermore, advantageously, said anti-reflux valve is capable of collaborating with fixing means of the device according to the invention, to improve and simplify the fixing of the first and second sheaths to said device.

What is more, to make it easier to visually monitor the release stage, for example through a transparent window in the casing, like the aforementioned one, at least one of said sheaths, preferably the intermediate sheath, advantageously has at least one graduation of the conventional type on its external face.

BRIEF DESCRIPTION OF THE DRAWINGS

The figures of the appended drawing will make it easy to understand how the invention may be embodied. In these figures, identical references denote similar elements.

DETAILED DESCRIPTION OF THE PREFERRED EMBODIMENTS

Figure 1:
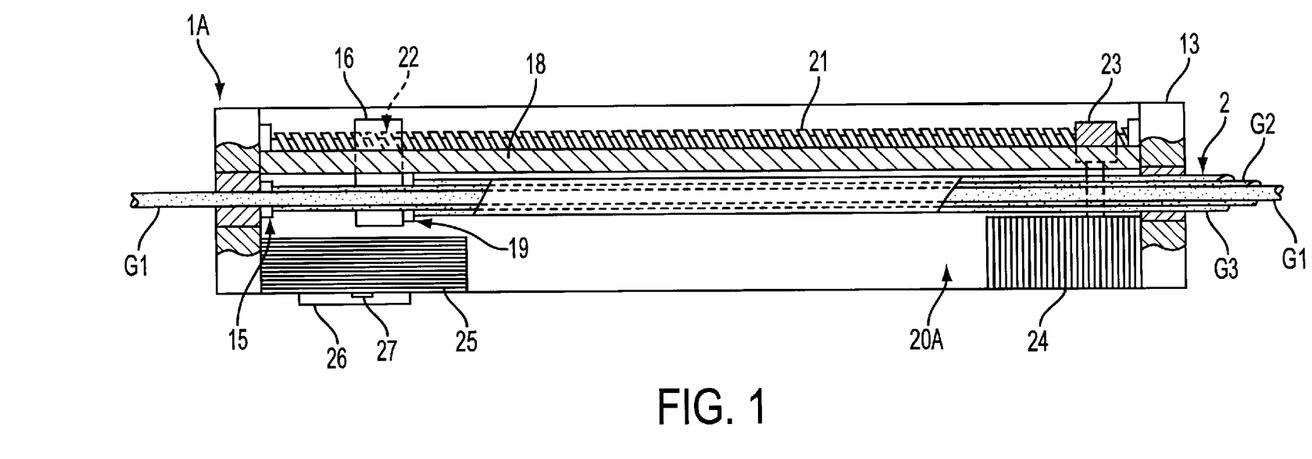
FIGS. 1 to 3 show a first embodiment of a device according to the invention, viewed respectively from the front, from above (the casing being open each time) and in perspective.
Figure 2:
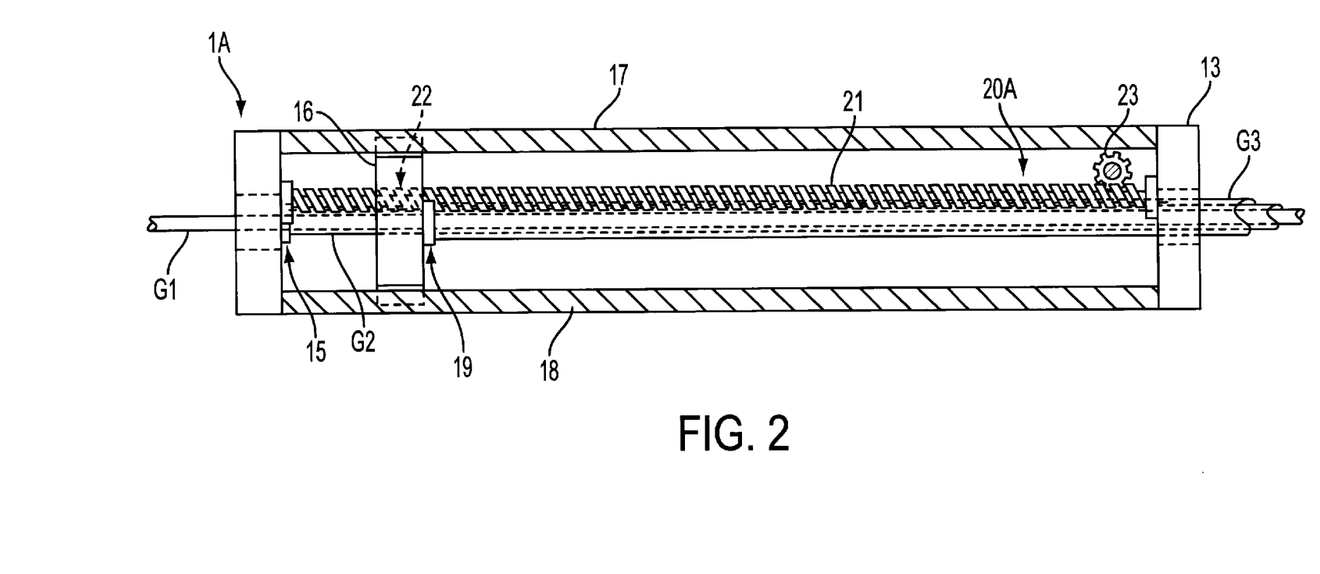
Figure 3:
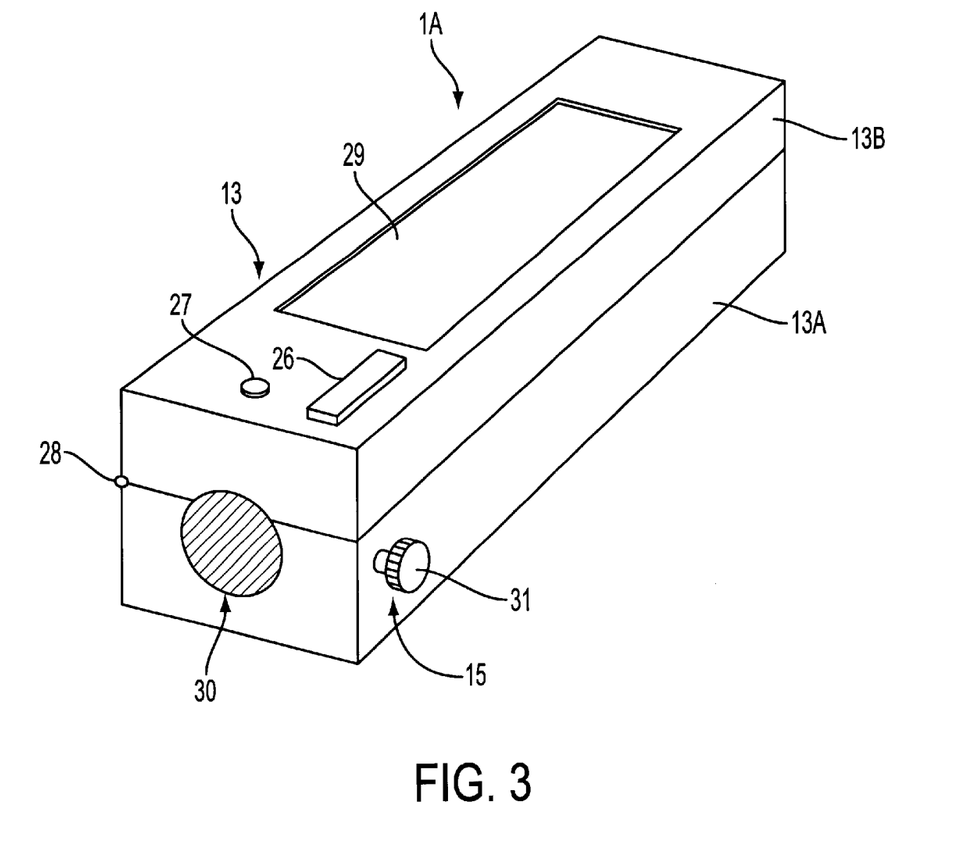

The device 1A, 1B, 1C, 1D according to the invention and depicted diagrammatically, in a first embodiment 1A, in FIGS. 1 to 3, is intended to cause the release of an object, particularly a prosthesis, into a human or animal passage.

Figure 4:
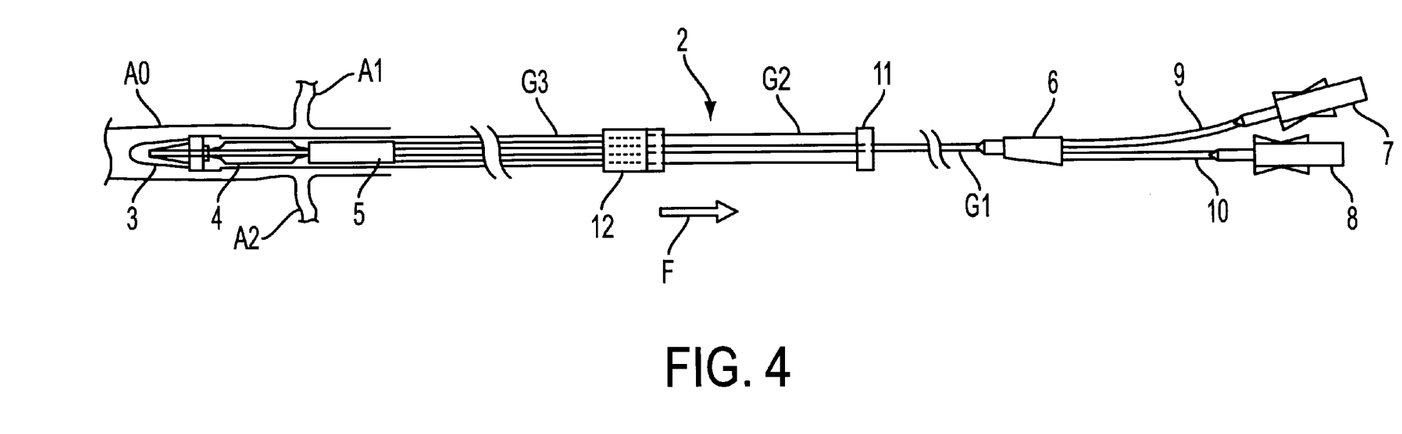
FIGS. 4 and 5 diagrammatically illustrate a catheter respectively in a position just prior to the release of the object and in a released position.
Figure 5:
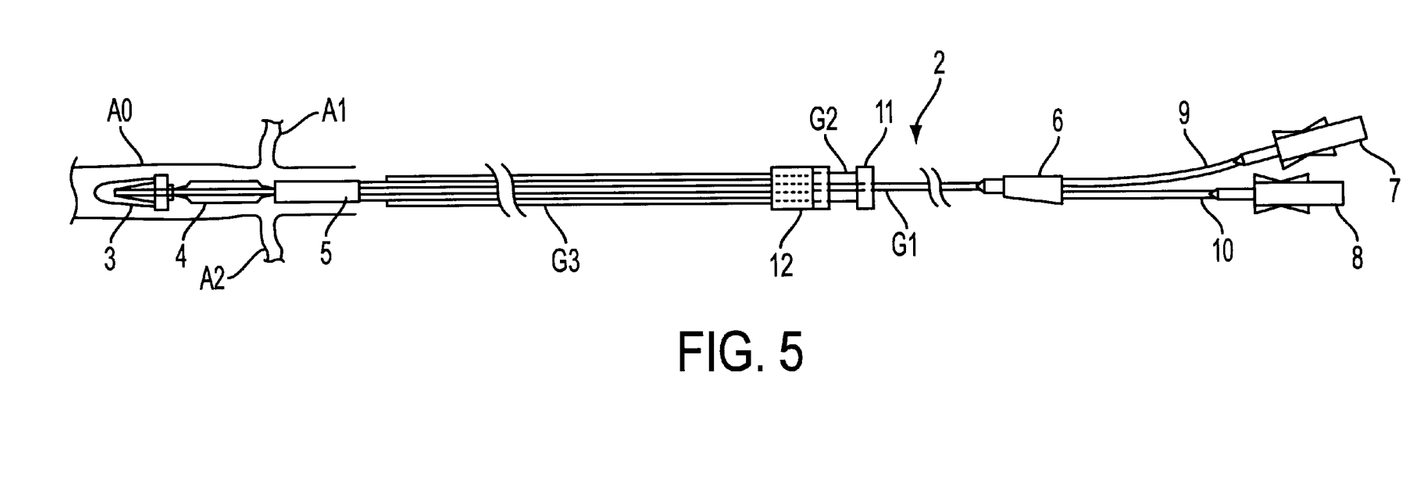

To this end, said device 1A, 1B, 1C, 1D is associated with a catheter 2 depicted in FIGS. 4 and 5 to form an implantation system according to the invention.

In the known way, such a catheter 2 or delivery system comprises a carrying sheath G1 which is produced in the form of a tube with twin openings which, at its distal part, comprises, in succession, a dilation tip 3, a dilation balloon 4 and a prosthesis 5 intended to be implanted in an artery AO of the human body, for example in the abdominal aorta, particularly at the junction with other arteries A1 and A2, for example the renal arteries.

Said carrying sheath G1 additionally comprises, at the proximal part, a branch connection means 6 to which two connecting means 7 and 8 of the known "luer lock" type are connected so as to create two lines 9 and 10, one for inflating the dilation balloon 4 and the other for stiffening the carrying sheath G1, for example using a metal rod, not depicted, inserted into said carrying sheath G1.

Said known catheter 2 also comprises:

an intermediate sheath G2 surrounding the sheath G1 in the distal part as far as the region of the prosthesis 5 and which can slide over said sheath G1; and a protective outer sheath G3 surrounding the sheath G2 in the distal part as far as the dilation tip 3 and which can slide over said sheath G2.

The sheaths G1 to G3 are thus mounted telescopically.

When implanting the prosthesis 5, the distal part of the catheter 2 is brought into the aorta AO in the known way so that the prosthesis 5 is at least near its future location, as illustrated in FIG. 4. Starting from this position, the prosthesis 5 has first of all to be released, then the catheter 2 has to be withdrawn from the human body.

In the known way, release is achieved by withdrawing or sliding the sheath G3 in the direction of the arrow F depicted in FIG. 4 with respect to the sheath G2, so as to uncover the distal part of the catheter 2 comprising, in particular, the balloon 4 and the prosthesis 5, as illustrated in FIG. 5.

Each of the sheaths G2 and G3 also has, at its proximal end, a collar 11, 12 specified hereinbelow and which, in particular, allows the corresponding sheath G2, G3 to be fixed respectively to the sheath G1, G2 inside it.

The device 1A, 1B, 1C, 1D is intended more specifically to withdraw or slide the sheath G3 with respect to the sheath G2 starting from the position illustrated in FIG. 4 so as to uncover and release the prosthesis 5, as depicted in FIG. 5.

More generally, said device 1A, 1B, 1C, 1D is intended to cause the relative sliding of two sheaths of a catheter so as to release any object carried by said catheter into a human or animal passage.

To this end, in order to create said relative sliding, it is conceivable, in a particular application of the invention, not depicted, for not the outer sheath G3, but the sheath G2 to be moved, by pushing it in said sheath G3.

According to the invention, said device 1A to 1D comprises, as depicted for example in FIGS. 1 to 3 in the first embodiment 1A:

a casing 13, 14 through which the catheter 2 can, at least partially, pass;

fixing means 15 specified hereinbelow for fixing an extracorporal part (in the positions of FIGS. 4 and 5) of the sheath G2, and preferably the collar 11 of this sheath G2 as specified hereinbelow, to said casing 13, 14;

a mobile carriage 16 mounted on said casing 13, 14 via guide rails 17 and 18;

fixing means 19 specified hereinbelow for fixing an extracorporal part (in the positions of FIGS. 4 and 5) of the sheath G3, preferably the collar 12 as indicated hereinbelow, to said mobile carriage 16; and controllable drive means 20A, 20B, 20C, 20D capable of moving said mobile carriage 16 with respect to said casing 13, 14.

In consequence, when he wishes to release the prosthesis 5 starting from the position, depicted in FIG. 4, of the catheter 2, said catheter 2 being connected to the device 1A to 1D according to the invention in the aforementioned way, the surgeon implanting the prosthesis 5, or one of his assistants, has simply to operate the drive means 20A, 20B, 20C and 20D. These then cause the mobile carriage 16 to move with respect to the casing 13, 14 and thus cause the relative sliding of said sheaths G3 and G2 which are fixed respectively to the mobile carriage 16 and to the casing 13, 14.

Release therefore occurs automatically, or at worst through the generation of a low force (depending on the embodiment of drive means 20A to 20D considered, as specified hereinbelow) with nothing in common with the force which would have had to be exerted by the surgeon without the use of the device according to the invention.

In consequence, by virtue of the invention, release is achieved:

smoothly and continuously, without jerkiness, allowing better control over the release stage and avoiding any risk of injuring the wall of the artery AO;

very precisely, it being possible, in particular, for the release stage to be monitored visually and/or by radiography, and for this stage even to be pre-programmed, as specified hereinbelow; and with no physical effort or, at most, with a very small physical effort on the part of the surgeon, even when the prosthesis 5 to be released is very large.

In the context of the present invention, the drive means may be embodied in different ways.

In the first embodiment 1A depicted in FIGS. 1 to 3, said drive means 20A comprise an endless screw 21 which is mounted on said casing 13, which collaborates with a tapping 22 made in the carriage 16 and which is moved by a gear wheel 23 driven by a motor 24, particularly an electric motor.

In the case of an electric motor 24, the latter may be powered with electricity either from the mains (not depicted) or using at least one battery 25. In this case, the casing 13 additionally comprises:

a switch 26, accessible from the outside, for controlling said motor 24; and a charge indicator 27 which may become illuminated or flash when the battery charge 25 drops below a predetermined level.

As can be seen in FIG. 3, the casing 13 is preferably made in two parts 13A and 13B connected by hinges 28, which allows a catheter 2 to be mounted easily in said casing 13 simply by pivoting the part 13B with respect to the part 13A to open said casing 13.

The casing 13 additionally comprises:

a transparent window 29 allowing the relative sliding of the sheaths G2 and G3 and therefore the release stage to be visually monitored. For this purpose, at least one of said sheaths G2, G3, preferably the sheath G2, has at least one conventional graduation on its external face; and openings 30 made longitudinally on each side of the casing 13 to allow the passage of the catheter 2, the diameters of said two openings 30 preferably being tailored to those of the sheaths G1 and G3 respectively.

In a particular embodiment, the fixing means 15 comprise a screw 31. In the context of the present invention, they can also comprise a clip or any other known fixing element, not depicted. The same is true of the fixing means 19.

As a preference, said fixing means 15 and 19 collaborate respectively with the collars 11 and 12, which are formed correspondingly, in order to fix the sheaths G2 and G3.

Said collars 11 and 12 additionally comprise anti-reflux valves so as to prevent any blood from flowing out of the artery AO via the catheter 2.

Figure 6:
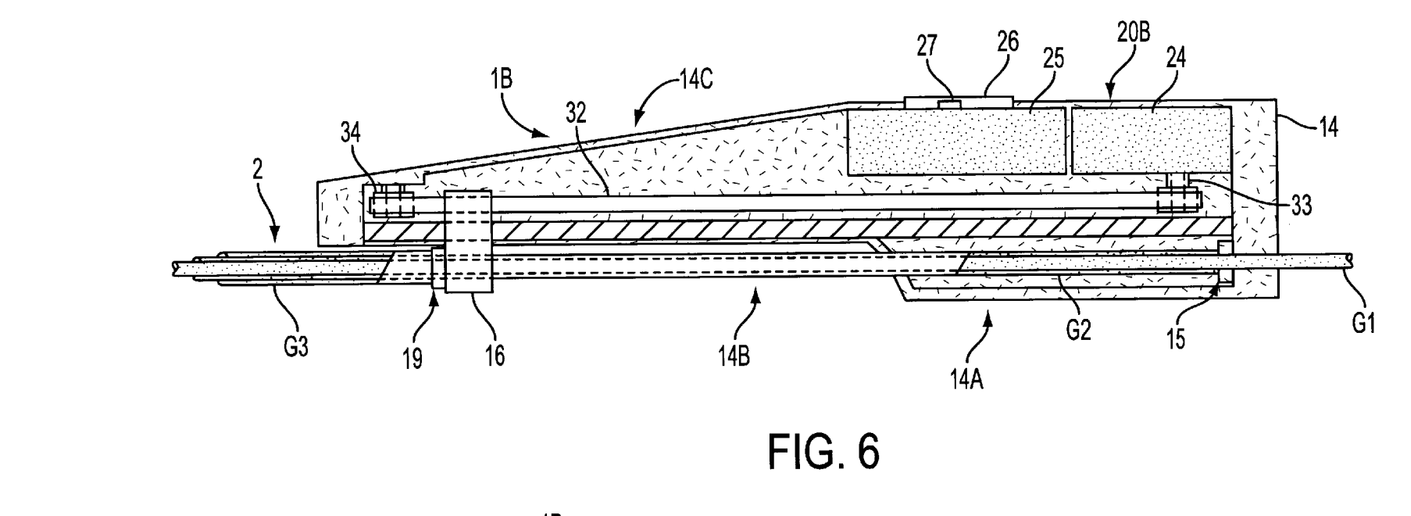
FIGS. 6 and 7 diagrammatically illustrate, viewed respectively from the front and from above (the casing being open each time), a second embodiment of a device according to the invention.
Figure 7:
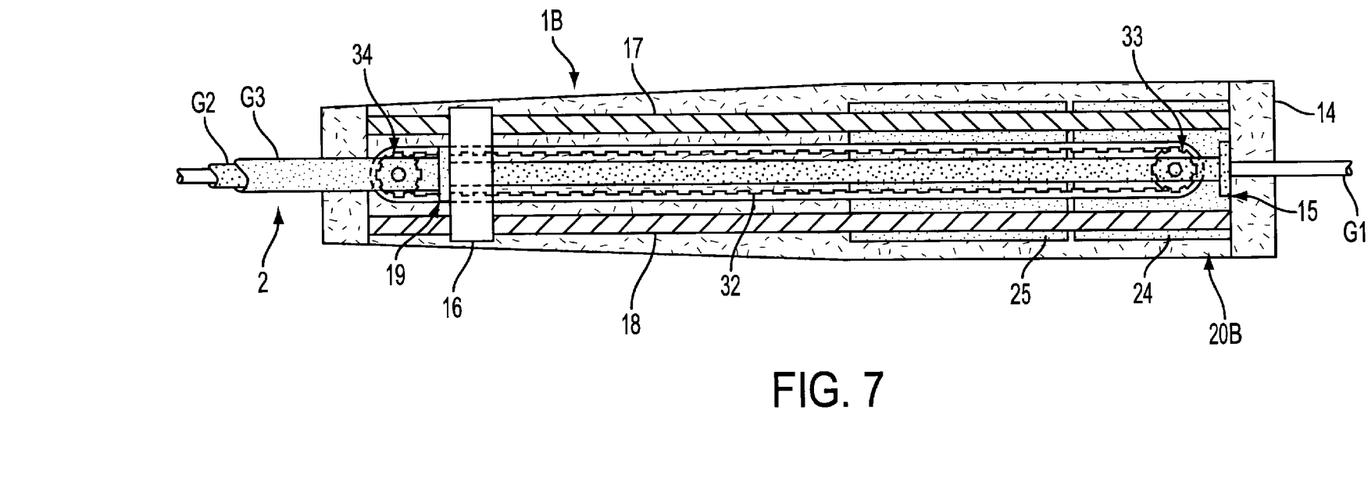

Furthermore, in the second embodiment 1B depicted in FIGS. 6 and 7, the drive means 20B comprise a rack system which comprises a rack or toothed belt 32 acting on the mobile carriage 16 formed appropriately, rotated by a toothed wheel 33 moved by the motor 24 and arranged between said moved toothed wheel 33 and a toothed wheel 34 which is free to rotate.

Furthermore, at one of its ends, the casing 14 has a handgrip region 14A tailored to the hand of a user of the device 1B, making this device easier to manipulate. At the other end of said casing 14, one 14C of the faces 14B, 14C is tapered and the other face 14B is formed in such a way that the carriage 16 is partially outside said casing 14, as partially are those parts of the sheaths G2 and G3 located between the collars 11 and 12, thus making it easier to visually monitor the relative sliding of said sheaths G2 and G3.

It will further be noted that, in embodiments 1A and 1B, the motor 24 may be controlled automatically by a programmable element, not depicted, for example an integrated electronic chip. Thus, the prosthesis 5 may be released automatically according to a pre-established program.

Figure 8:
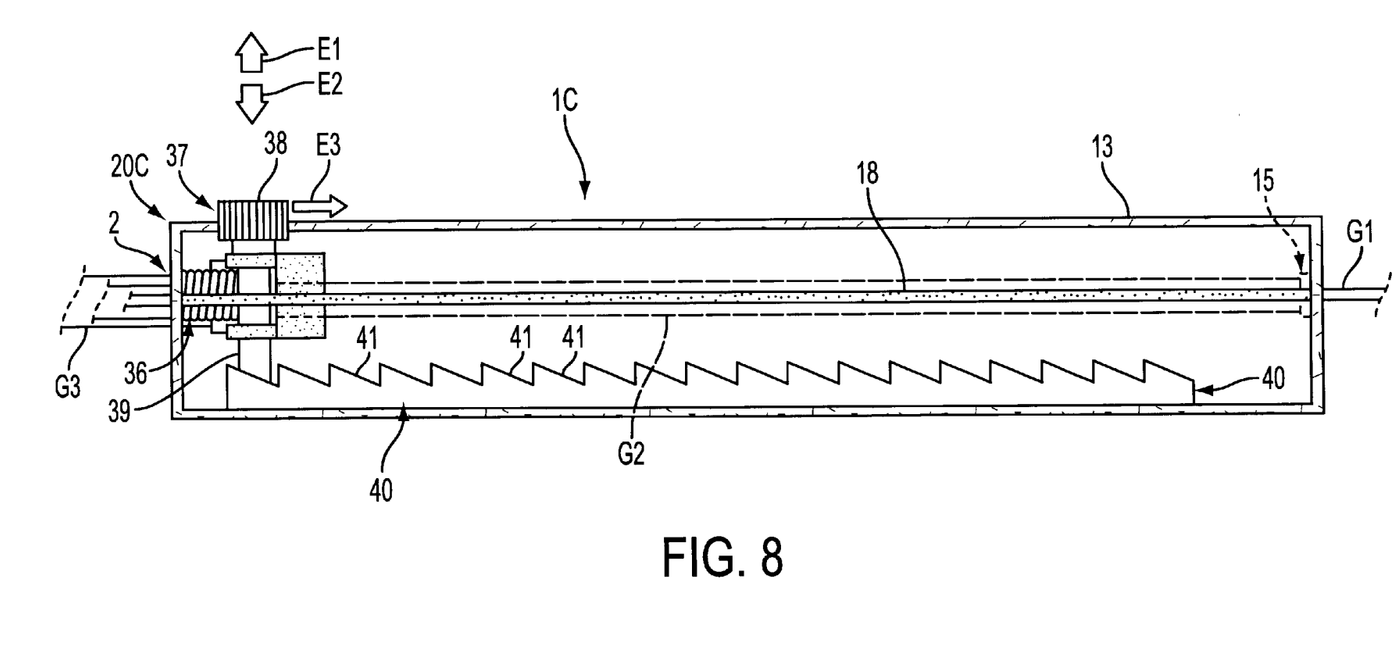
FIGS. 8 and 9 diagrammatically illustrate a device according to the invention in, respectively, a third and a fourth embodiment.

Furthermore, in the third embodiment 1C depicted in FIG. 8, the drive means 20C comprise:

an elastic means 36, preferably a spring, which is mounted so that it is elastically constrained between the casing 13 and the mobile carriage 16 and which is capable of making said mobile carriage 16 slide along the guide rails 18; and a controllable stop 37, capable of preventing said mobile carriage 16 from moving with respect to said casing 13.

In a particular embodiment as depicted, said stop 37 comprises a knob 38 which can be pulled or pushed, as illustrated by arrows E1 and E2 respectively. This knob 38 is secured to a rigid tongue 39 capable of acting on a toothed (or notched) strip 40 which is fixed to the bottom of the casing 13. The free end of said tongue 39 is tapered to suit the shape of the teeth 41 on the said strip 40.

When, starting out from the position depicted in FIG. 8, the knob 38 is pulled in the direction of the arrow E1, the tongue 39 is released from the strip 40 so that the stop for the carriage 16 is unlocked. It is then made to move in the direction of the arrow E3 under the action of the elastic means 36 until it reaches the opposite end or until the knob 38 is pushed back in the direction of the arrow E2.

Figure 9:
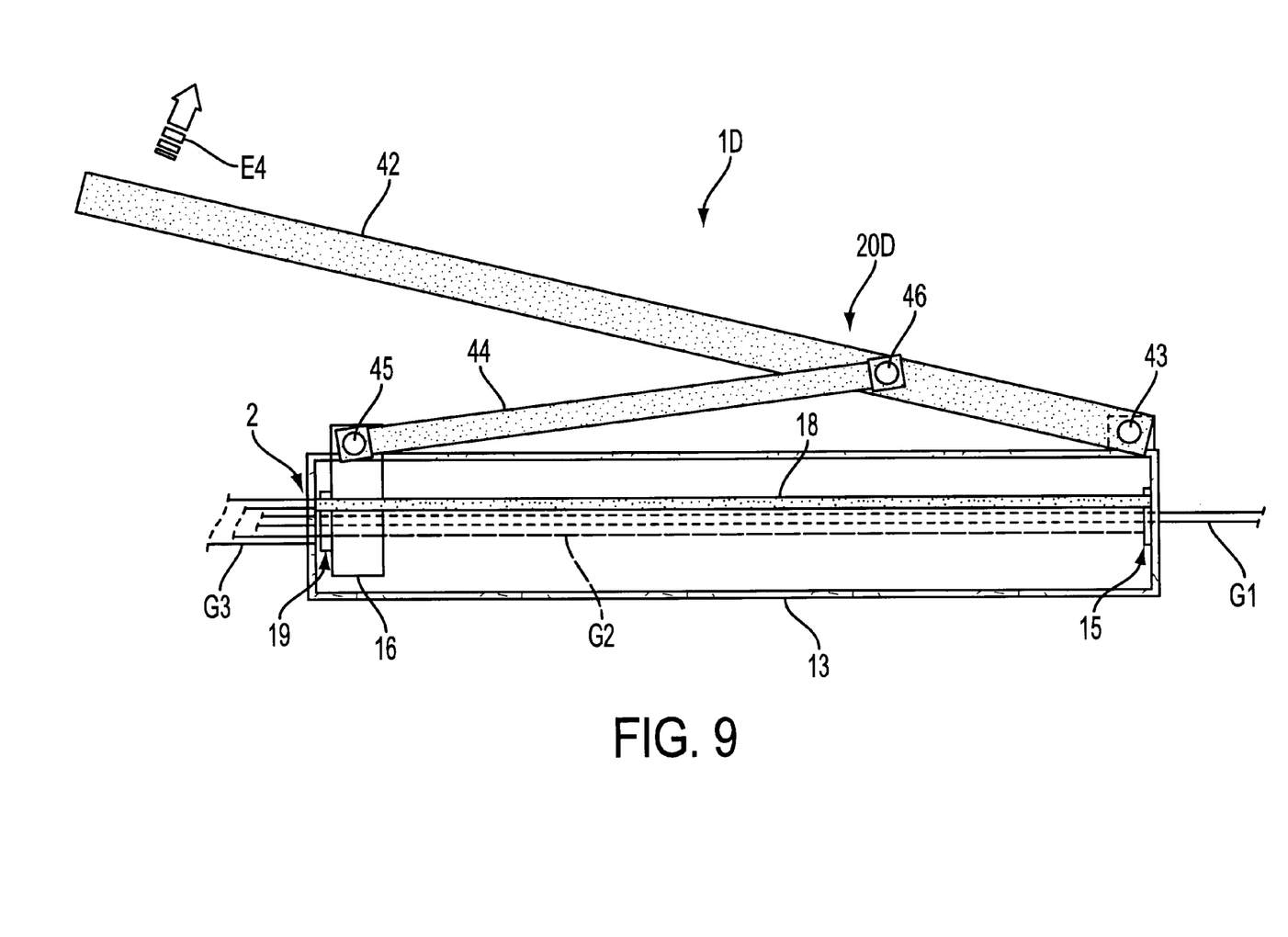

Furthermore, in the fourth and last embodiment 1D depicted in FIG. 9, the drive means 20D comprise a lever system which comprises:

a lever 42 which can be actuated, as illustrated by an arrow E4, and which is mounted so that it pivots on the casing 13 via a pivot 43; and an intermediate arm 44 mounted so that it is articulated to the carriage 16 and the lever 42 by articulations 45 and 46, respectively.

In consequence, and as is clearly apparent from FIG. 9, a movement or actuation, preferably by hand, of the free end of the lever 42 causes the carriage 16 to move, by means of the arm 44. It will be noted that even when the aforementioned actuation is performed manually, the force that has to be exerted on the lever 42 remains very small, particularly because of the lever arm effect obtained by virtue of the invention.

What is claimed is:

1. A device for causing the release of an object into a human or an animal passage, the object for being carried and delivered into the passage by a catheter which comprises a first sheath and a second sheath which are mounted slidably and telescopically with respect to each other, the catheter for being at least partially inserted into the passage to release the object in response to relative sliding of said first and second sheaths, said device comprising:

a casing;

a first fixing means for fixing an extracorporal part of said first sheath to said casing;

a mobile carriage mounted on said casing and being movable with respect to the casing;

a second fixing means for fixing an extracorporal part of said second sheath to said mobile carriage;

a controllable drive means comprising a motor for moving said mobile carriage with respect to said casing; and a programmable element for automatically controlling the motor to release the object according to a pre-established program.

2. The device as claimed in claim 1, wherein said drive means further comprise an endless screw for engaging a tapping formed in said carriage and wherein the screw is moved by the controllable motor.

3. The device as claimed in claim 1, wherein said drive means further comprise a rack system which acts on said carriage and which is moved by said controllable motor.

4. The device as claimed in claim 1, wherein said casing has a transparent window which allows part of at least one of said sheaths located inside said casing to be seen from outside the casing.

5. The device as claimed in claim 1, wherein said casing is made in two parts which are at least partially separable and which can be secured together.

6. The device as claimed in claim 1, wherein said casing has an elongate shape comprising a handgrip region tailored to be gripped by a hand of someone using said device.

7. A device for causing the release of an object into a human or an animal passage, the object for being carried and delivered into the passage by a catheter which comprises a first sheath and a second sheath which are mounted slidably and telescopically with respect to each other, the catheter for being at least partially inserted into the passage to release the object in response to relative sliding of said first and second sheaths, said device comprising:

a casing;

a first fixing means for fixing an extracorporal part of said first sheath to said casing;

a mobile carriage mounted on said casing and being movable with respect to the casing;

a second fixing means for fixing an extracorporal part of said second sheath to said mobile carriage;

a controllable drive means comprising a motor for moving said mobile carriage with respect to said casing; and guide rails secured to said casing and wherein said carriage is mounted so that it can move on said guide rails.

8. The device as claimed in claim 7, wherein said drive means further comprise an endless screw for engaging a tapping formed in said carriage and wherein the screw is moved by the controllable motor.

9. The device as claimed in claim 7, wherein said drive means further comprise a rack system which acts on said carriage and which is moved by said controllable motor.

10. The device as claimed in claim 7, wherein said casing has a transparent window which allows part of at least one of said sheaths located inside said casing to be seen from outside the casing.

11. The device as claimed in claim 7, wherein said casing is made in two parts which are at least partially separable and which can be secured together.

12. A system for implanting an object in a human or an animal passage, said system comprising:

a catheter for carrying and delivering the object into the passage and including a first sheath and a second sheath which are mounted slidably and telescopically with respect to one another, the catheter for being inserted at least partially into the passage and for releasing the object in response to relative sliding of said first and second sheaths; and a device for releasing the object in the passage, the device including:

a casing;

a first fixing means for fixing an extracorporal part of said first sheath to said casing;

a mobile carriage mounted on said casing and being movable with respect to the casing;

a second fixing means for fixing an extracorporal part of said second sheath to said mobile carriage; and a controllable drive means comprising a motor for moving said mobile carriage with respect to said casing, wherein at least one of said sheaths comprises an anti-reflux valve.

13. The system as claimed in claim 12, wherein said anti-reflux valve is for cooperating with at least one of the first fixing means and the second fixing means of said device for releasing said object.

14. The system as claimed in claim 12, wherein at least one of said sheaths has at least one graduation on an external face thereof.

15. A device for causing the release of an object into a human or an animal passage, the object for being carried and delivered into the passage by a catheter which comprises a first sheath and a second sheath which are mounted slidably and telescopically with respect to each other, the catheter for being at least partially inserted into the passage to release the object in response to relative sliding of said first and second sheaths, said device comprising:

a casing;

a first fixing means for fixing an extracorporal part of said first sheath to said casing;

a mobile carriage mounted on said casing and being movable with respect to the casing;

a second fixing means for fixing an extracorporal part of said second sheath to said mobile carriage; and a controllable drive means comprising a motor for moving said mobile carriage with respect to said casing, wherein said motor is an electric motor for being powered by a battery, and wherein said casing comprises a switch for controlling said motor and a charge indicator which one of illuminates or flashes when the battery drops below a predetermined level.

16. The device as claimed in claim 15, wherein said drive means further comprise an endless screw for engaging a tapping formed in said carriage and wherein the screw is moved by the controllable motor.

17. The device as claimed in claim 15, wherein said drive means further comprise a rack system which acts on said carriage and which is moved by said controllable motor.

18. The device as claimed in claim 15, wherein said casing has a transparent window which allows part of at least one of said sheaths located inside said casing to be seen from outside the casing.

19. The device as claimed in claim 15, wherein said casing is made in two parts which are at least partially separable and which can be secured together.

20. A system for implanting an object in a human or animal passage, comprising:

a catheter for carrying and delivering the object into the passage and including:

a first sheath and a second sheath mounted slidably and telescopically relative to one another, the catheter for being inserted at least partially into the passage and for releasing the object in response to relative sliding of the first and second sheaths, and an anti-reflux valve disposed within at least one of the first or second sheaths; and a device for releasing the object in the passage, the device including:

a casing;

a first fixing means for fixing an extracorporal part of the first sheath to the casing;

a mobile carriage mounted on the casing and movable with respect to the casing;

a second fixing means for fixing an extracorporal part of the second sheath to the mobile carriage; and a controllable motor for moving the mobile carriage with respect to the casing.

21. The system as in claim 20, wherein the anti-reflux valve is for cooperating with at least one of the first or second fixing means of the device for releasing the prosthesis.

22. The system as claimed in claim 20, wherein the object is a prosthesis.

* * * * *